US009613728B2

(12) United States Patent
Brauss

(10) Patent No.: US 9,613,728 B2
(45) Date of Patent: Apr. 4, 2017

(54) X-RAY DIFFRACTION APPARATUS AND METHOD

(71) Applicant: Proto Manufacturing Ltd., Oldcastle (CA)

(72) Inventor: E. Michael Brauss, Amherstburg (CA)

(73) Assignee: Proto Manufacturing Ltd., Ontario (CA)

( * ) Notice: Subject to any disclaimer, the term of this patent is extended or adjusted under 35 U.S.C. 154(b) by 205 days.

(21) Appl. No.: 14/213,047

(22) Filed: Mar. 14, 2014

(65) Prior Publication Data
US 2014/0270090 A1    Sep. 18, 2014

Related U.S. Application Data

(60) Provisional application No. 61/801,250, filed on Mar. 15, 2013.

(51) Int. Cl.
*G01N 23/20* (2006.01)
*G21K 1/06* (2006.01)
*G01N 23/207* (2006.01)

(52) U.S. Cl.
CPC ............ *G21K 1/06* (2013.01); *G01N 23/207* (2013.01); *G01N 23/20008* (2013.01); *G01N 2223/056* (2013.01)

(58) Field of Classification Search
CPC ............ G01N 23/20; G01N 23/20008; G01N 23/20016; G01N 23/205; G01N 2223/05; G01N 2223/056; G01N 2223/30; G01N 2223/308; G01N 2223/321; G01N 2223/3303; G01N 2223/3305
See application file for complete search history.

(56) References Cited

U.S. PATENT DOCUMENTS

| 2,640,159 A | * | 5/1953 | Gerneth | .................. A61N 5/01 250/492.1 |
| 2,695,362 A | * | 11/1954 | Gerneth | ............... A61B 6/0407 378/179 |
| 2,947,214 A | | 8/1960 | Schwuttke et al. | |
| 3,082,322 A | * | 3/1963 | Koerner | .................. A61N 5/01 378/196 |

(Continued)

FOREIGN PATENT DOCUMENTS

| EP | 2472252 A1 | 4/2012 | |
| FR | 2830613 | 4/2011 | |
| GB | 686828 A * | 2/1953 | ............... A61N 5/01 |

OTHER PUBLICATIONS

European Search Report from corresponding European Patent Application No. 14160214.4 dated Nov. 4, 2014, 7 pages.

(Continued)

*Primary Examiner* — Thomas R Artman
(74) *Attorney, Agent, or Firm* — Fitch, Even, Tabin & Flannery LLP

(57) ABSTRACT

An x-ray diffraction apparatus is provided having an x-ray diffraction head, a frame for supporting the x-ray diffraction head, and a pair of drive mechanisms of the frame configured to generate pivotal movement of the x-ray diffraction head about first and second orthogonal axes. The frame is configured such that operation of one of the drive mechanisms to rotate the x-ray diffraction head about the first axis generates rotation of both of the drive mechanisms about the first axis.

36 Claims, 8 Drawing Sheets

(56) References Cited

U.S. PATENT DOCUMENTS

| | | | | |
|---|---|---|---|---|
| 3,322,948 A * | 5/1967 | Baak | G01N 23/207 | 378/71 |
| 3,394,255 A * | 7/1968 | Furnas, Jr. | G01N 23/207 | 378/71 |
| 3,639,758 A * | 2/1972 | Shimura | G01N 23/207 | 378/124 |
| 3,714,426 A * | 1/1973 | Wolfel | G01N 23/205 | 378/77 |
| 3,728,541 A * | 4/1973 | Rabinovich | G01N 23/20025 | 378/77 |
| 3,868,506 A | 2/1975 | Ogiso | | |
| 4,134,020 A * | 1/1979 | Zonneveld | A61B 6/032 | 378/13 |
| 4,149,079 A * | 4/1979 | Ben-Zeev | A61B 6/032 | 378/14 |
| 4,199,678 A * | 4/1980 | Ladell | G01N 23/207 | 378/75 |
| 5,014,292 A * | 5/1991 | Siczek | A61B 6/00 | 378/195 |
| 5,187,729 A * | 2/1993 | Ibe | G01N 23/20008 | 356/31 |
| 5,367,554 A * | 11/1994 | Kobayashi | A61B 6/00 | 378/196 |
| 5,515,416 A * | 5/1996 | Siczek | A61B 6/4014 | 378/196 |
| 5,966,423 A * | 10/1999 | Quinn | G01N 23/20025 | 378/79 |
| 6,005,914 A * | 12/1999 | Quinn | G01N 23/20025 | 378/79 |
| 6,064,717 A | 5/2000 | Ortega et al. | | |
| 6,072,854 A * | 6/2000 | Kikuchi | C30B 15/00 | 378/71 |
| 6,418,190 B1 * | 7/2002 | Yokozawa | G01N 23/20 | 378/73 |
| 6,621,085 B1 * | 9/2003 | Cipriani | H05H 7/00 | 250/442.11 |
| 6,721,393 B1 * | 4/2004 | Brauss | G01N 23/20016 | 378/196 |
| 6,751,287 B1 * | 6/2004 | Kalyon | G01N 15/1456 | 378/71 |
| 6,778,850 B1 * | 8/2004 | Adler | A61B 6/12 | 378/4 |
| 6,853,706 B2 * | 2/2005 | Brauss | G01N 23/20016 | 378/196 |
| 6,859,520 B2 * | 2/2005 | He | G01N 23/20016 | 378/71 |
| 6,925,146 B2 * | 8/2005 | Brauss | G01N 23/20008 | 378/71 |
| 6,927,399 B2 * | 8/2005 | Cipriani | H05H 7/00 | 250/440.11 |
| 6,965,661 B2 * | 11/2005 | Kojima | A61B 6/037 | 378/10 |
| 6,969,194 B1 * | 11/2005 | Nafstadius | A61N 5/01 | 378/197 |
| 6,976,784 B2 * | 12/2005 | Kojima | A61B 6/037 | 378/197 |
| 7,085,347 B2 * | 8/2006 | Mihara | A61N 5/10 | 378/197 |
| 7,242,744 B2 | 7/2007 | Brauss | | |
| 7,260,178 B2 * | 8/2007 | Berti | G01N 23/207 | 250/305 |
| 7,283,612 B2 | 10/2007 | Brausss | | |
| 8,536,547 B2 * | 9/2013 | Maurer, Jr. | A61N 5/1081 | 250/492.1 |
| 2002/0191734 A1 * | 12/2002 | Kojima | A61B 6/037 | 378/4 |
| 2003/0219099 A1 * | 11/2003 | He | G01N 23/20016 | 378/70 |
| 2004/0037390 A1 * | 2/2004 | Mihara | A61N 5/10 | 378/65 |
| 2004/0165697 A1 * | 8/2004 | Brauss | G01N 23/20016 | 378/71 |
| 2004/0174948 A1 * | 9/2004 | Kojima | A61B 6/037 | 378/19 |
| 2004/0184580 A1 * | 9/2004 | Brauss | G01N 23/20008 | 378/70 |
| 2005/0098737 A1 * | 5/2005 | Cipriani | H05H 7/00 | 250/442.11 |
| 2005/0195942 A1 * | 9/2005 | Brauss | G01N 23/20016 | 378/81 |
| 2005/0281375 A1 * | 12/2005 | Brauss | G01N 23/20008 | 378/81 |
| 2007/0071170 A1 * | 3/2007 | Brauss | G01N 23/20008 | 378/81 |
| 2012/0189102 A1 * | 7/2012 | Maurer, Jr. | A61N 5/1081 | 378/65 |
| 2014/0009741 A1 * | 1/2014 | Levien | A61B 3/102 | 351/206 |
| 2014/0039303 A1 * | 2/2014 | Kanzaki | A61B 6/12 | 600/424 |

OTHER PUBLICATIONS

Rigaku, AutoMATE: Micro-Area X-ray Stress Measurement System, publicly available more than one year before Mar. 15, 2013, 3 pages.

* cited by examiner

X-RAY DIFFRACTION APPARATUS AND METHOD

CROSS-REFERENCE TO RELATED APPLICATION

This application claims the benefit of U.S. Provisional Patent Application No. 61/801,250, filed Mar. 15, 2013, which is hereby incorporated by reference in its entirety.

FIELD OF THE INVENTION

The invention relates to an apparatus and method for measuring strength-related characteristics of a part using x-ray diffraction techniques and, more particularly, to an apparatus and method for measuring the strength-related characteristics at a variety of positions relative to the part.

BACKGROUND

The use of x-ray diffraction techniques for measuring residual stresses in crystalline substances such as metal or ceramic materials is well-known. The general idea with the use of x-ray diffraction is to subject the material to the radiation of x-rays with the resulting sensed x-ray diffraction peak interpreted to arrive at a measurement of a strength related characteristic, e.g. stress, retained austenite, and hardness of the part material. Some x-ray diffraction instruments have an x-ray head that is moved about the part so that measurements can be taken across a sufficient number of positions on the part to obtain information therefrom.

For example, the x-ray diffraction head of some prior x-ray diffraction instruments have a depending collimator tube with a lower end through which x-rays are emitted toward a part being analyzed. The x-ray diffraction head is pivoted about an Ω axis and moved in an arcuate path around a χ axis during analysis of the part. The Ω and χ axes intersect perpendicular to one another at a distal end of the collimator tube. However, these prior x-ray diffraction instruments utilize complicated drive structures to provide the movement of the x-ray head about the χ and Ω axes. The complicated structures may limit the size of parts that can be analyzed by the x-ray diffraction instruments in order to provide the desired movement of the x-ray diffraction head about the χ and Ω axes.

DETAILED DESCRIPTION

In accordance with one aspect, an x-ray diffraction apparatus is provided having an x-ray diffraction head, a frame for supporting the x-ray diffraction head, and a pair of drive mechanisms of the frame configured to generate pivotal movement of the x-ray diffraction head about respective first and second axes defined by the drive mechanisms. The frame is configured such that operation of one of the drive mechanisms to pivot the x-ray diffraction head about the first axis generates pivoting of both of the drive mechanisms about the first axis.

In one form, the frame includes an arcuate guide having a center of curvature intersected by the first axis. The frame includes a drive frame, such as a carriage, connected to the arcuate guide and having the x-ray diffraction head and both drive mechanisms mounted thereto. One of the drive mechanisms is configured to advance the carriage along the arcuate guide which produces movement of both drive mechanisms along the arcuate guide and about the first axis. The first axis may be a χ axis of the x-ray diffraction apparatus and the second axis may be a Ω axis of the x-ray diffraction apparatus.

Figure 1:
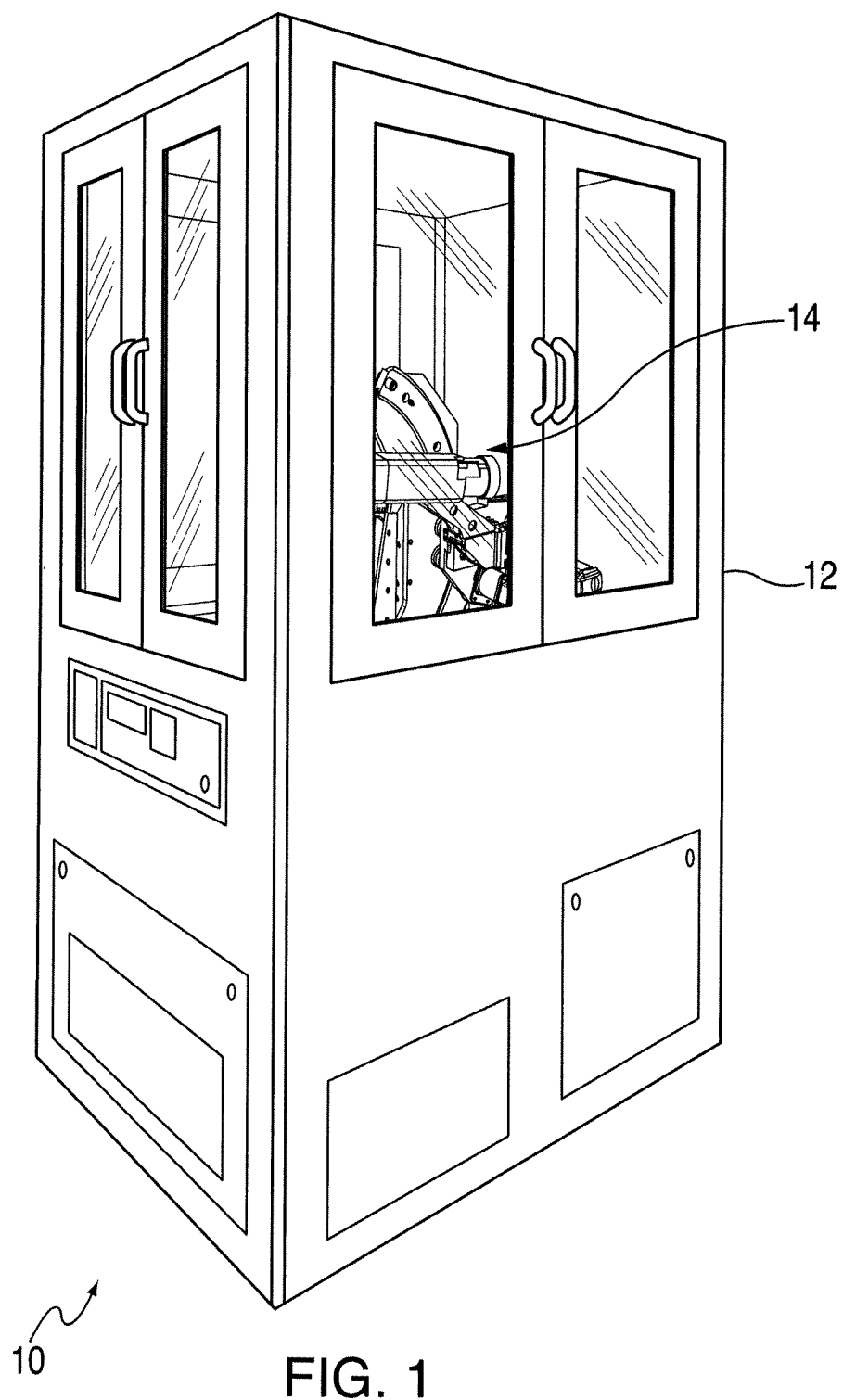
FIG. 1 is a perspective view of an x-ray diffraction instrument having an x-ray diffraction apparatus disposed within a compartment of the x-ray diffraction instrument.
Figure 2:
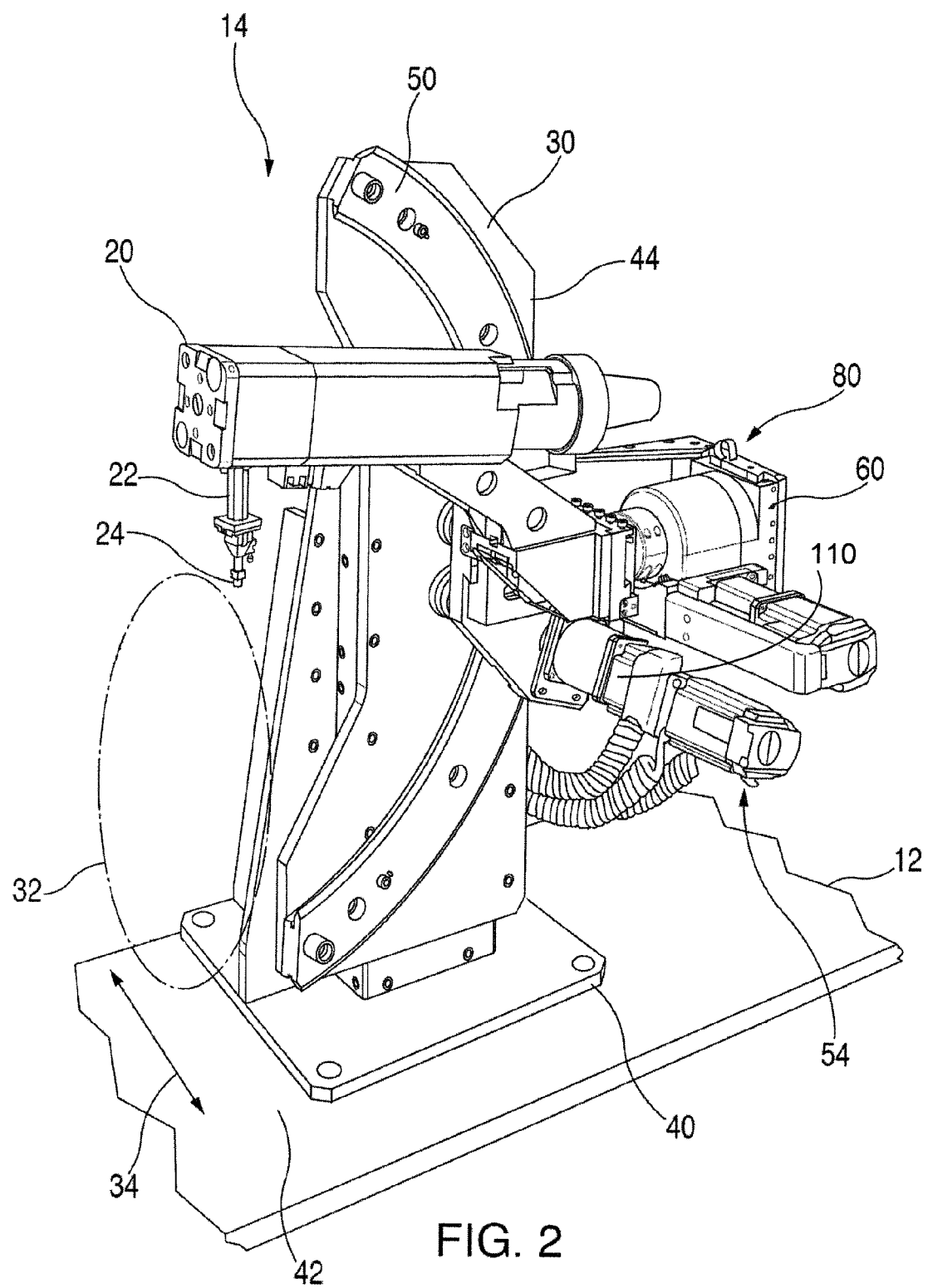
FIG. 2 is a perspective view of the x-ray diffraction apparatus of FIG. 1 showing a mounting portion of the apparatus secured to a table of the compartment.

With reference to FIGS. 1 and 2, an x-ray diffraction instrument 10 having an enclosed compartment 12 that includes an x-ray diffraction apparatus 14 therein is shown. The x-ray diffraction instrument 10 can analyze larger parts than some prior x-ray diffraction instruments because the x-ray diffraction 14 imposes fewer spacial constraints on the part being analyzed.

More specifically, the x-ray diffraction apparatus 14 has an elongated x-ray diffraction head 20 with a collimator 22 and a distal end 24 thereof which directs x-rays toward the part being analyzed. The apparatus 14 has a frame 30 for supporting the x-ray diffraction head 20 and providing an enlarged part receiving area 32 on a side of the apparatus 14 that may be larger than the part-receiving areas of some prior instruments. The frame 30 provides an unobstructed path 34 for loading and unloading parts into the part receiving area 32. Further, the frame 30 may take up less space within the compartment 12 than the frames of prior x-ray diffraction instruments which can restrict the ability of an operator to load larger parts into the prior instruments.

Figure 3:
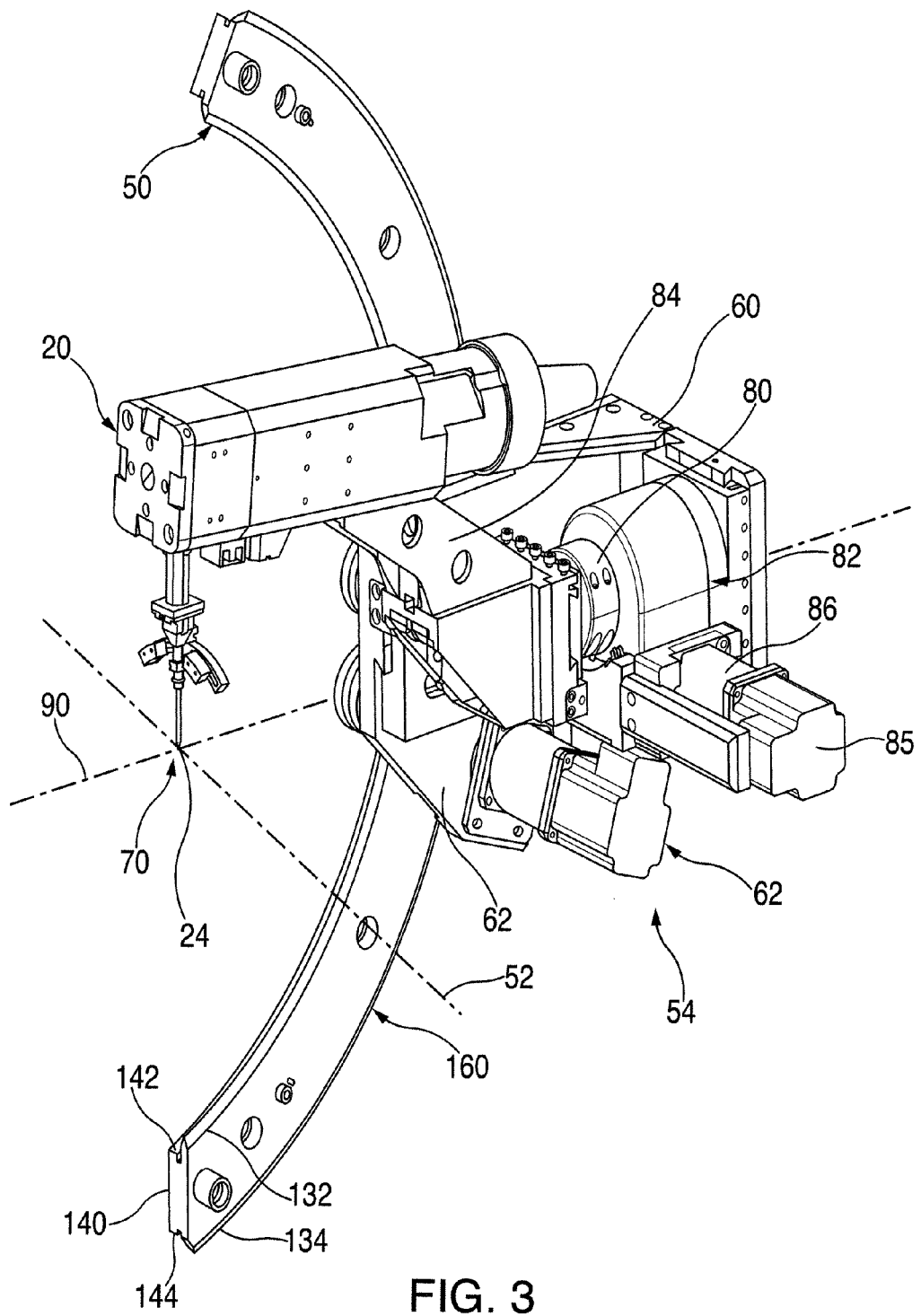
FIG. 3 is a perspective view of the x-ray diffraction apparatus of FIG. 2 showing an x-ray head of the apparatus mounted on a carriage configured to travel along an arcuate rack.
Figure 8:
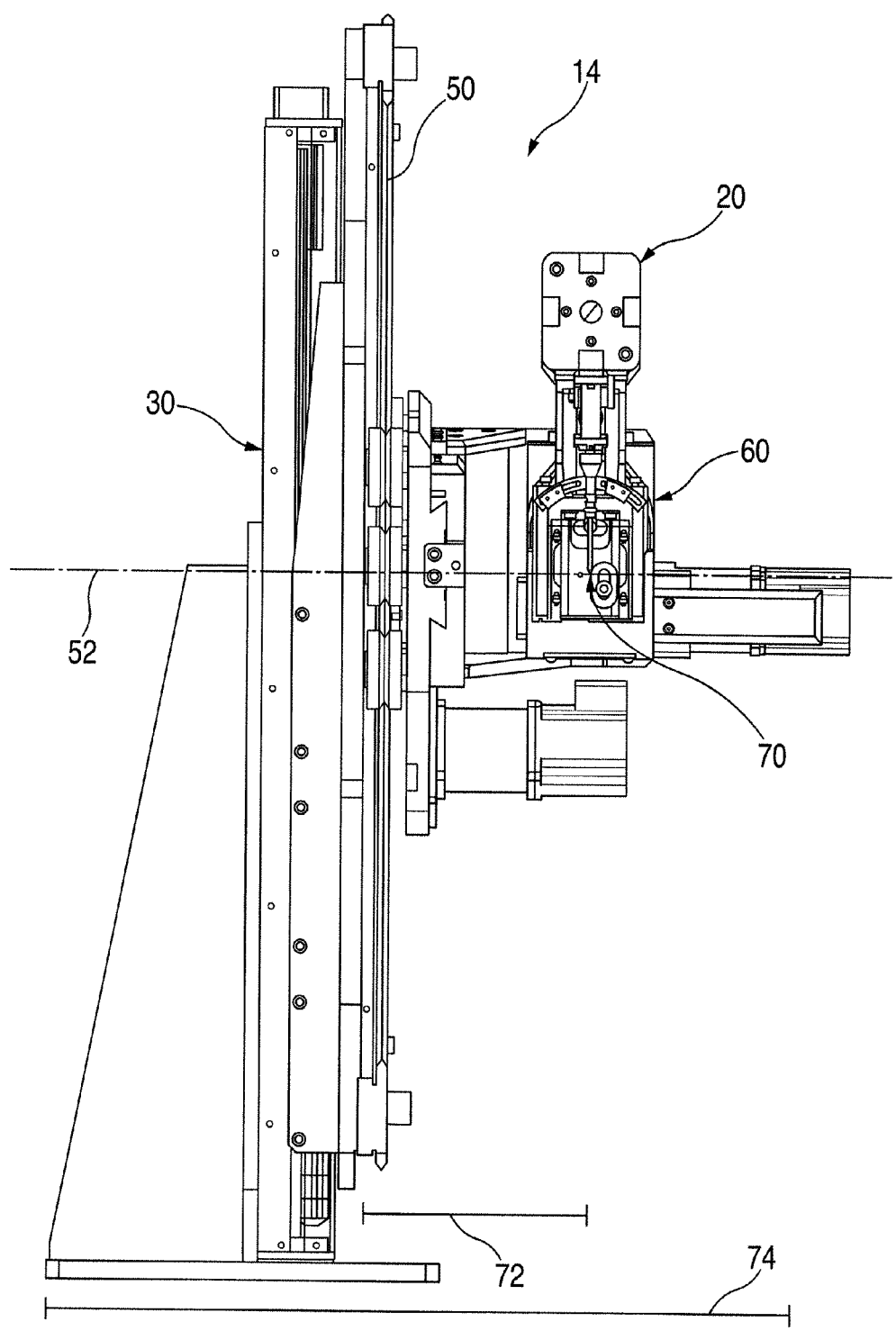
FIG. 8 is a side elevational view of the x-ray diffraction apparatus of FIG. 2 showing the carriage extending outwardly from the rack.

The frame 30 has a base mounting portion 40 secured to a table 42 of the instrument compartment 12 and a relatively narrow or thin width support portion 44 upstanding from the base mounting portion 40 within the compartment 12. The support portion 44 includes an arcuate rack 50 that curves around a center of curvature 70 aligned on a χ axis 52 of rotation for the x-ray diffraction head 20, as shown in FIGS. 3 and 8. The frame 30 is configured to provide a compact distance 72 between the rack 50 and the center of rotation 70 so that the overall depth 74 of the apparatus 14 within the compartment 12 can be minimized, as shown in FIG. 8.

With reference to FIG. 3, the frame 30 includes an adjustable mount 54 for oscillating the x-ray head 20 about the χ axis 52 and along the arcuate rack 50. The adjustable mount 54 includes a carriage 60 with a drive mechanism 62 operable to move the carriage 60 along the arcuate rack 50. In one form, the drive mechanism 62 includes a rack-and-pinion mechanism for selectively advancing the carriage 60 along the arcuate rack 50.

The frame 30 includes a second adjustable mount 80 for oscillating the x-ray head 20 about an Ω axis 90 that perpendicularly intersects the χ axis 52 at the center of rotation 70, as shown in FIG. 3. The adjustable mount 80 includes a drive mechanism 82 coupled to a bracket 84 to which the x-ray head 20 is mounted. The drive mechanism 82 may include a motor 85 operable to turn a screw drive 86 which drives gearing configured to produce rotary movement of the x-ray head 20 generally centered about the Ω axis 90.

Figure 4:
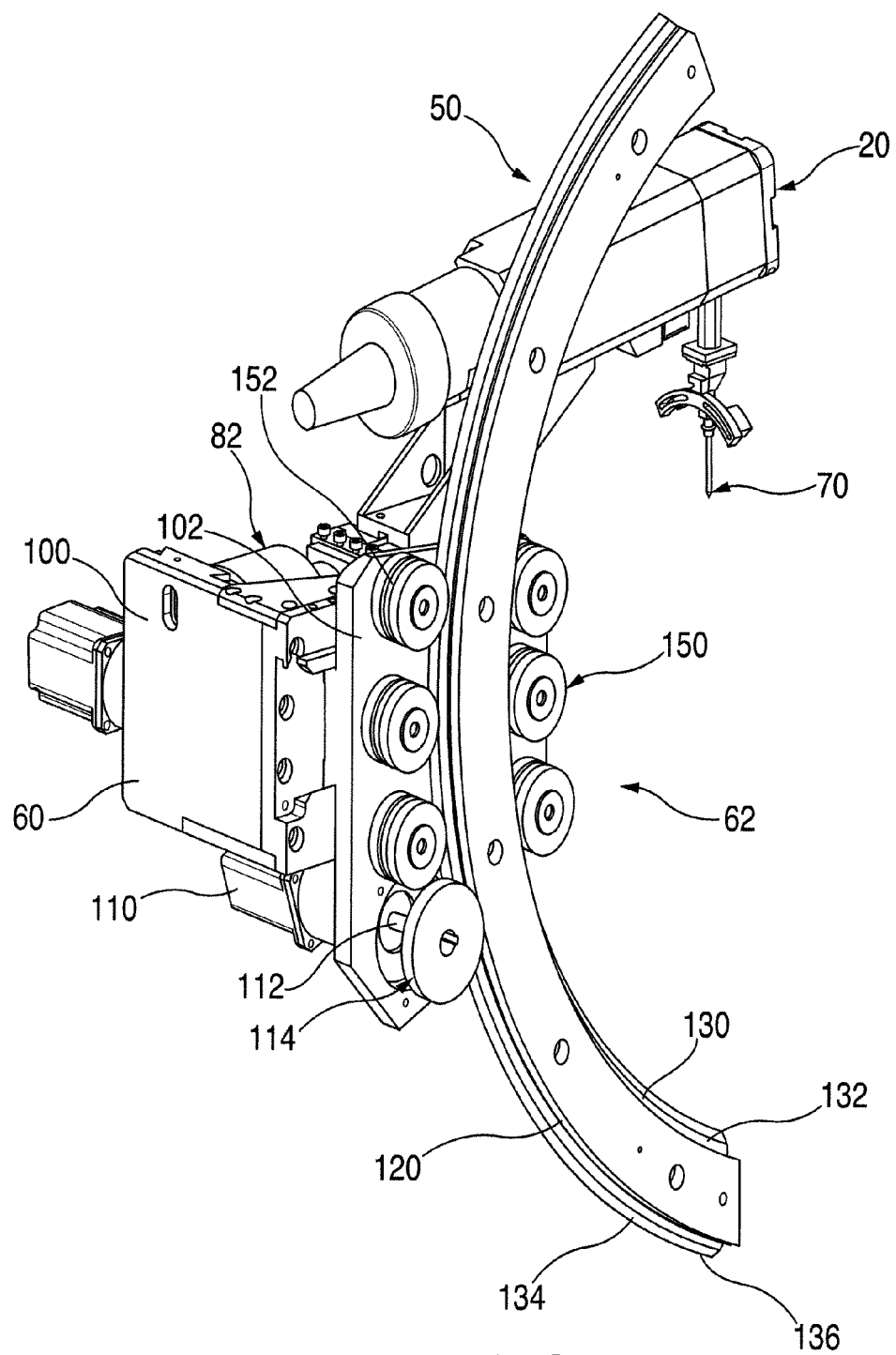
FIG. 4 is a perspective view of the x-ray diffraction apparatus of FIG. 2 showing a drive gear and rollers of the carriage engaged with the arcuate rack.

With reference to FIG. 4, the carriage 60 has a support plate 100 to which the Ω-axis drive mechanism 82 is mounted and a transmission plate 102 to which the χ-axis drive mechanism 62 is mounted. Thus, the carriage 60 has both the χ-axis drive mechanism 62 and the Ω axis drive mechanism 82 mounted thereto. In this manner, neither of the drive mechanisms 62 or 82 or support structure therefor interfere with substantially a full range of rotary movements of the x-ray head 20 about the axes 52 and 90 enabling the x-ray head 20 to take x-ray diffraction measurements from parts with complex geometries such as gear teeth, or the like.

In particular, the χ-axis drive mechanism 62 includes a motor 110 secured to the transmission plate 102 with a drive shaft 112 extending therefrom. The χ-axis drive mechanism 62 includes a drive gear 114 fixed to the drive shaft 112 and the arcuate rack 50 includes outer gear teeth 120 arranged therealong configured to engage the drive gear 114.

With reference to FIG. 4, the rack 50 has an inner portion 130 with a radially inwardly extending rail 132 and an outer portion 134 with radially outwardly extending rail 136 disposed laterally and radially outward from the gear teeth 120. The χ-axis drive mechanism 62 is configured to engage and travel along the rails 132, 136, which function to resist twisting movement of the carriage 60 about the rack 50 and maintain the substantially perpendicular orientation of the elongated x-ray diffraction head 20 relative to the χ-axis 52.

With reference to FIG. 3, the rack 50 includes a rectangular body portion 140 with inner and outer surfaces 142, 144 thereof and the rails 132, 134 extend beyond the outer surfaces 142, 144. In one form, the rack gear teeth 120 are formed in the surface 144 and are configured to engage the drive gear 114 of the carriage 60.

With reference to FIG. 4, the carriage 60 includes sets of grooved rollers 150 on opposite sides of the rack 50 and rotatably mounted to the transmission plate 102. The rollers 150 include circumferential channels or grooves 152 configured to receive the rails 132, 134 therein and thereby engage the carriage 60 to the inner and outer portions 130, 134 of the rack 50. The engagement of the rollers 150 with the inner and outer portions 130, 134 of the rack 50 constrains the carriage 60 to oscillatory arcuate movement along the rack 50 about the χ axis 52.

Figure 5:
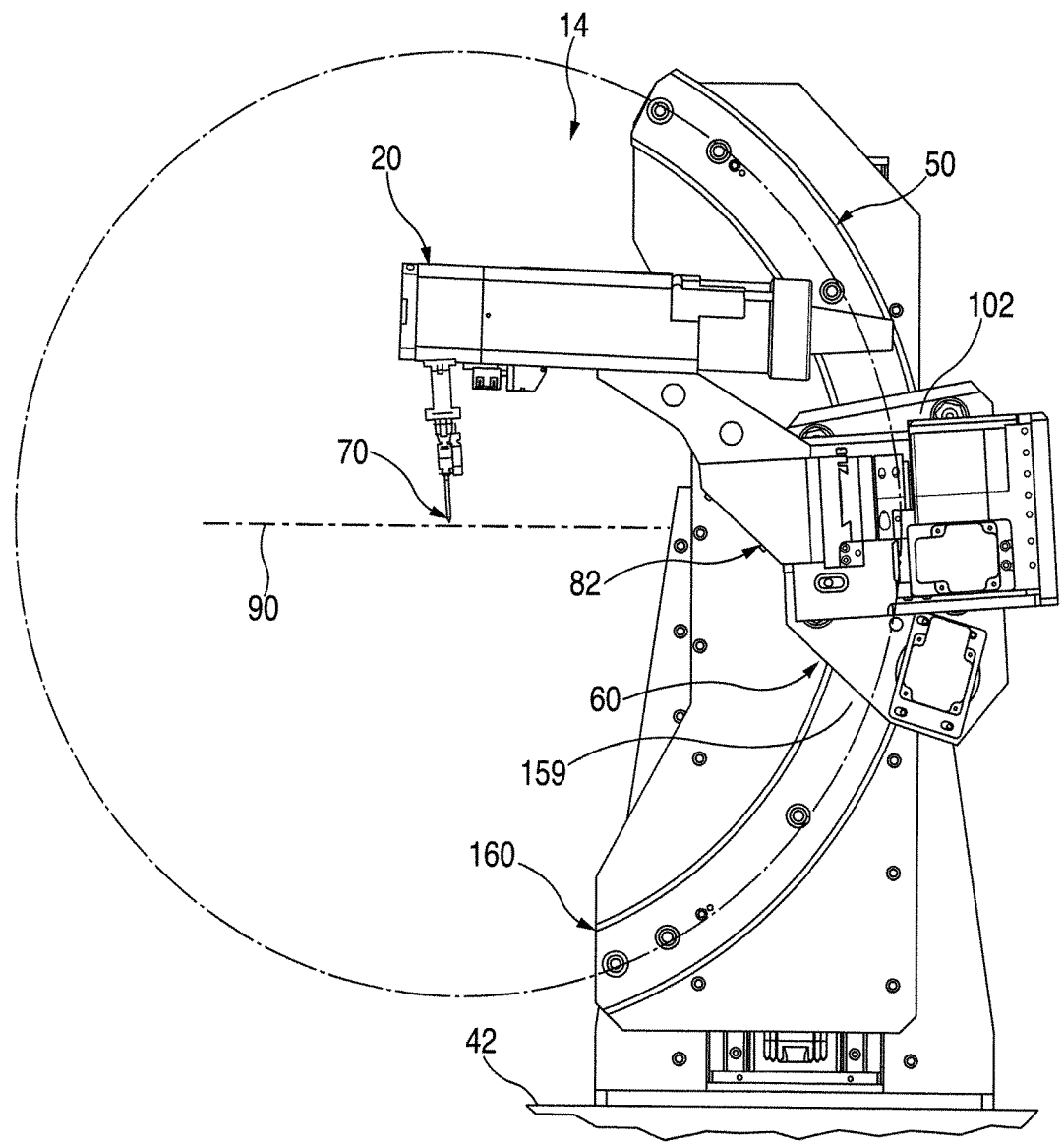
FIG. 5 is an elevational view of the x-ray diffraction apparatus of FIG. 2 showing the carriage at a position along the arcuate rack that orients a Ω-axis of rotation of the x-ray diffraction head at a zero degree angle generally parallel to the compartment table.
Figure 6:
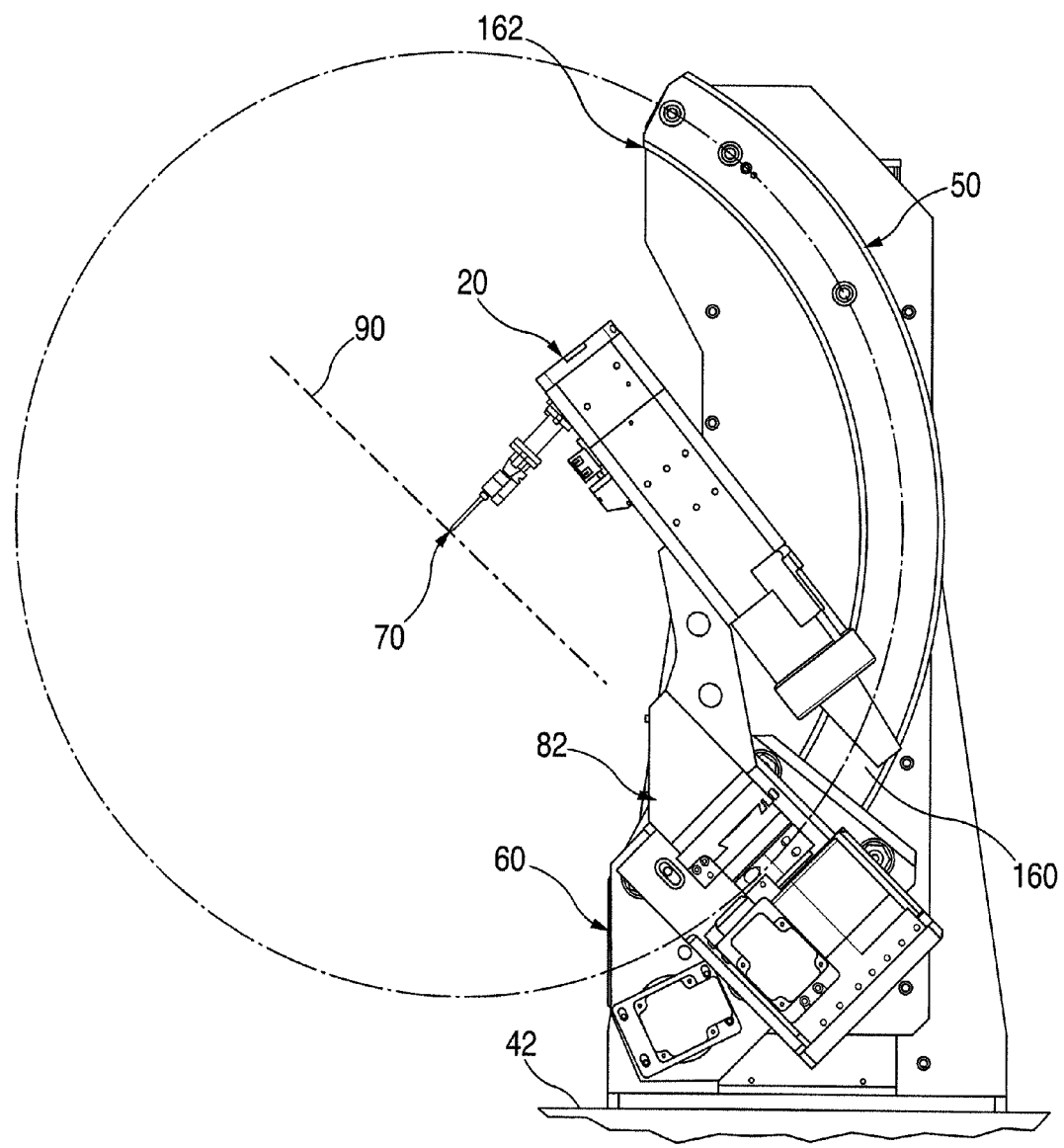
FIG. 6 is an elevational view similar to FIG. 5 showing the carriage moved along the rack to orient the Ω-axis to extend at a negative forty-five-degree angle relative to the compartment table.
Figure 7:
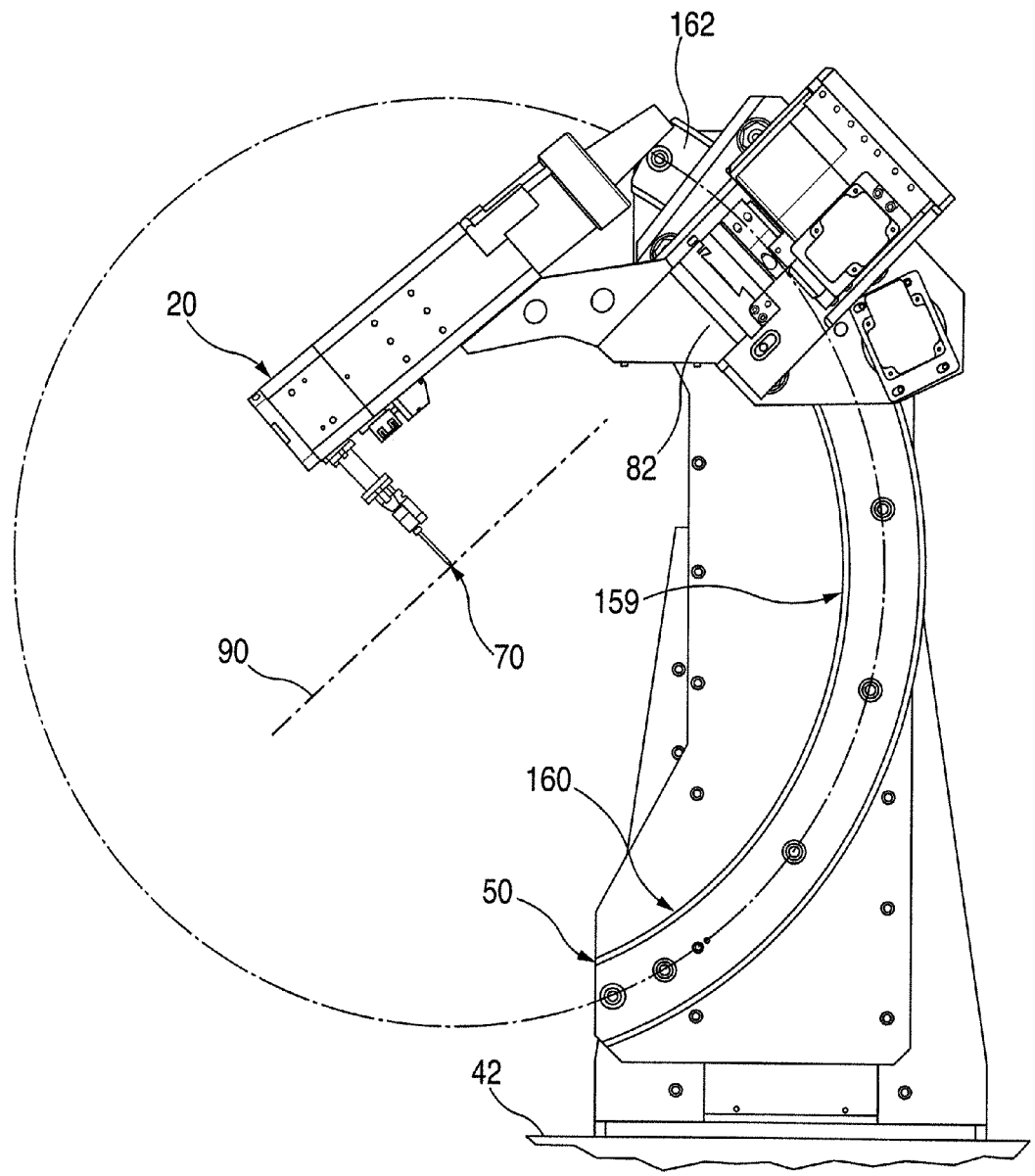
FIG. 7 is an elevational view showing the carriage moved about the rack toward an opposite end of the rack which orients the Ω-axis to extend at a positive forty-five degree angle relative to the compartment table.

With reference to FIGS. 5-7, the movement of the carriage 60 and x-ray head 20 mounted thereto is shown. With reference to FIG. 5, the carriage 60 is shown disposed at a central portion 159 of the rack 50 in a zero-degree position about the χ axis such that the Ω axis 90 defined by the Ω-axis drive mechanism 82 is oriented to extend generally parallel to the compartment table 42. To move the x-ray diffraction head 20 about the χ-axis 52 (see FIGS. 3 and 8), the χ-axis drive mechanism 62 can be operated to rotate the drive gear 114 and advance the carriage 60 toward a lower end portion 160 of the rack 50. As shown in FIG. 6, the arcuate rack 50 causes the carriage 60 and the Ω-axis drive mechanism 82 connected thereto to be oriented such that the Ω-axis defined by the drive mechanism 82 is oriented to extend at a negative forty-five degree angle. The χ-axis drive mechanism 62 can also be operated to cause the drive gear 114 to rotate in a reverse direction and advance the carriage 60 toward an upper portion 162 of the rack 50, as shown in FIG. 7. In this position, the arcuate rack 50 causes the carriage 60 and Ω-axis drive mechanism 82 connected thereto to be oriented such that the Ω-axis extends at a positive forty-five degree angle relative to the compartment table 42.

While there have been illustrated and describe particular embodiments of the present invention, it will be appreciated that numerous changes and modifications will occur to those skilled in the art and is intended that all those changes and modifications fall within the true spirit and scope of the present invention.

What is claimed is:

1. An x-ray diffraction apparatus comprising:
   an x-ray head;
   a frame for supporting the x-ray head;
   a first drive mechanism of the frame configured to move the x-ray head about a first axis;
   a collimator of the x-ray head configured to emit x-rays in a direction transverse to the first axis;
   a second drive mechanism of the frame configured to move the x-ray head, the first drive mechanism, and the second drive mechanism together about a second axis generally perpendicular to the first axis; and
   a sensor adapted to sense diffracted x-rays after the x-rays have been emitted from the collimator.

2. The x-ray diffraction apparatus of claim 1 wherein the frame includes an arcuate guide member extending about the second axis and the second drive mechanism is configured to shift the x-ray head, the first drive mechanism, and the second drive mechanism together along the arcuate guide member.

3. The x-ray diffraction apparatus of claim 1 wherein the frame includes an arcuate guide member and a carriage configured for shifting along the arcuate guide member with the x-ray head being mounted to the carriage.

4. The x-ray diffraction apparatus of claim 3 wherein the second drive mechanism is configured to drive the carriage and x-ray head mounted thereto along the arcuate guide member.

5. The x-ray diffraction apparatus of claim 3 wherein the first drive mechanism and the second drive mechanism are mounted to the carriage and shiftable along the arcuate guide member.

6. The x-ray diffraction apparatus of claim 1 wherein the frame includes a rack and the second drive mechanism includes a rotatable driven member engaged with the rack such that rotation of the driven member drives the x-ray head, first drive mechanism, and second drive mechanism along the rack.

7. The x-ray diffraction apparatus of claim 1 wherein the frame includes a guide member and a carriage connected to the guide member for shifting therealong and extending to one side of the guide member with the x-ray head being mounted to the carriage to be spaced from the guide member on the one side thereof.

8. The x-ray diffraction apparatus of claim 7 wherein the first drive mechanism is mounted to the carriage to be spaced from the guide member on the one side thereof.

9. The x-ray diffraction apparatus of claim 1 wherein the frame includes a guide member and a carriage shiftable along the guide member with the x-ray head and first and second drive mechanisms mounted to the carriage; and
   a roller assembly of the carriage engaged with the guide member for rolling movement along the guide member with operation of the second drive mechanism.

10. The x-ray diffraction apparatus of claim 9 wherein the guide member has an arcuate configuration with a radius of curvature and a center of the radius of curvature is intersected by the second axis.

11. The x-ray diffraction apparatus of claim 1 wherein the frame includes an arcuate guide member and a carriage with the first drive mechanism mounted to the carriage, the carriage being connected to the arcuate guide member for shifting to predetermined positions therealong including:
   an upper position with the carriage shifted along the guide member such that the first axis extends at a positive forty five degree angle,
   an intermediate position with the carriage shifted along the guide member such that he first axis extends at a zero degree angle, and
   a lower position with the carriage shifted along the guide member such that the first axis extends at a negative forty five degree angle.

12. The x-ray diffraction apparatus of claim 1 wherein the first axis is an Ω-axis of the x-ray diffraction apparatus and the second axis is a χ-axis of the x-ray diffraction apparatus.

13. The x-ray diffraction apparatus of claim 1 wherein the frame includes an arcuate guide member having a constant radius of curvature and a carriage having the x-ray diffraction head thereon configured for shifting along the arcuate guide member.

14. An x-ray diffraction apparatus comprising:
   an elongated, arcuate guide member having a radius of curvature;
   a carriage mounted to the arcuate guide member for being moved about a predetermined guide axis extending through a center of the radius of curvature of the arcuate guide member;
   an x-ray head mounted to the carriage;
   a first drive mechanism mounted to the carriage for moving the x-ray head relative to the carriage about a predetermined x-ray head axis generally perpendicular to the guide axis which permit the x-ray head to be moved to different positions relative to the carriage; and
   a second drive mechanism configured to drive the carriage and the x-ray head mounted thereto about the guide axis; and
   a sensor adapted to sense diffracted x-rays after the x-rays have been emitted from the x-ray head.

15. The x-ray diffraction apparatus of claim 14 wherein the carriage is mounted to the arcuate guide member for shifting therealong and the second drive mechanism is configured to drive the carriage, the x-ray head, and the first drive mechanism along the arcuate guide member and about the guide axis.

16. The x-ray diffraction apparatus of claim 14 wherein the carriage includes a roller assembly engaged with the arcuate guide member for rolling movement along the guide with operation of the second drive mechanism.

17. The x-ray diffraction apparatus of claim 14 wherein the carriage includes a plurality of rotatable members engaged with the arcuate guide member on opposite sides of the arcuate guide member.

18. The x-ray diffraction apparatus of claim 14 wherein the arcuate guide member includes a rack and the second drive mechanism includes a rotatable driven member engaged with the rack such that operation of the second drive mechanism drives the carriage about the guide axis.

19. The x-ray diffraction apparatus of claim 14 wherein one of the carriage and the arcuate guide member includes a groove and the other of the carriage and the arcuate guide member includes a rail engaged with the groove.

20. The x-ray diffraction apparatus of claim 14 wherein one of the carriage and the arcuate guide member includes a pair of grooves and the other of the carriage and the arcuate guide member includes a pair of rails engaged with the grooves on opposite sides of the arcuate guide member.

21. The x-ray diffraction apparatus of claim 14 wherein the second drive mechanism is carried on the carriage and is configured to drive the carriage, the x-ray head, the first drive mechanism, and the second drive mechanism about the guide axis.

22. An x-ray diffraction apparatus comprising:
   an elongated, arcuate guide member extending about a lateral axis;
   a carriage mounted to the arcuate guide member and shiftable therealong;
   an x-ray head mounted to the carriage laterally from the arcuate guide member on one lateral side thereof;
   a drive mechanism mounted to the carriage and configured to move the x-ray head about an x-ray head axis generally perpendicular to the lateral axis; and
   a sensor adapted to sense diffracted x-rays have been emitted from the x-ray head.

23. The x-ray diffraction apparatus of claim 22 wherein the drive mechanism is mounted to the carriage laterally from the arcuate guide on the one lateral side thereof.

24. The x-ray diffraction apparatus of claim 22 Further comprising another drive mechanism mounted to the carriage and configured to shift the carriage along the arcuate guide member.

25. The x-ray diffraction apparatus of claim 24 wherein the other drive mechanism is mounted to the carriage laterally from the arcuate guide on the one lateral side thereof.

26. The x-ray diffraction apparatus of claim 22 wherein the carriage includes a roller assembly for rolling movement along the arcuate guide member with movement of the carriage along the guide member.

27. A method of operating an x-ray diffraction apparatus, the method comprising:
   operating a first motor to move an x-ray head about a first axis; and
   operating a second motor to move the x-ray head, the first motor, and the second motor together about a second axis generally perpendicular to the first axis.

28. The method of claim 27 wherein operating the second motor includes shifting the x-ray head, the first motor, and the second motor along an arcuate guide member.

29. The method of claim 27 wherein operating the second motor includes shifting a carriage carrying the x-ray head and the first motor along an arcuate guide member.

30. The method of claim 27 wherein operating the second motor includes rotating a driven member engaged with a rack and driving the x-ray head, first motor, and second motor along the rack.

31. The method of claim 27 wherein operating the second motor includes moving the x-ray head, first motor, and second motor to an upper position so that the first axis extends at an approximately positive forty-five degree angle.

32. The method of claim 27 wherein operating the second motor includes moving the x-ray head, first motor, and second motor to an intermediate position so that the first axis extends at an approximately zero degree angle.

33. The method of claim 27 wherein operating the second motor includes moving the x-ray head, first motor, and second motor to a lower position so that the first axis extends at an approximately negative forty-five degree angle.

34. The method of claim 27 further comprising emitting x-rays from a collimator of the x-ray head toward a part in a direction transverse to the first axis.

35. An x-ray diffraction apparatus comprising:
an elongated, arcuate guide member extending about a lateral axis;
a carriage mounted to the arcuate guide member and shiftable therealong;
an x-ray head mounted to the carriage laterally from the arcuate guide member on one lateral side thereof;
a drive mechanism mounted to the carriage and configured to move the x-ray head about an x-ray head axis generally perpendicular to the lateral axis; and
wherein the drive mechanism includes a motor disposed laterally from the arcuate guide member farther than the x-ray diffraction head.

36. An x-ray diffraction apparatus of comprising:
an elongated, arcuate guide member extending about a lateral axis;
a carriage mounted to the arcuate guide member and shiftable therealong;
an x-ray head mounted to the carriage laterally from the arcuate guide member on one lateral side thereof;
a drive mechanism mounted to the carriage and configured to move the x-ray head about an x-ray head axis generally perpendicular to the lateral axis; and
wherein the carriage includes a transmission plate having a first side facing the one side of the arcuate guide member and a second side facing away from the one side of the arcuate guide member with the x-ray head being mounted to the second side of the transmission plate.

* * * * *

UNITED STATES PATENT AND TRADEMARK OFFICE
CERTIFICATE OF CORRECTION

PATENT NO. : 9,613,728 B2
APPLICATION NO. : 14/213047
DATED : April 4, 2017
INVENTOR(S) : E. Michael Brauss Page 1 of 1

It is certified that error appears in the above-identified patent and that said Letters Patent is hereby corrected as shown below:

In the Claims

Claim 14, Column 5, Line 50, delete "permit" and insert -- permits --, therefor.
Claim 22, Column 6, Line 32, after "head" insert -- relative to the carriage --.
Claim 22, Column 6, Line 34, after "x-rays" insert -- after the x-rays --.
Claim 24, Column 6, Line 39, delete "Further" and insert -- further --, therefor.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*